(12) United States Patent
Weckstrom

(10) Patent No.: US 6,716,637 B2
(45) Date of Patent: Apr. 6, 2004

(54) CHEMILUMINESCENT GAS ANALYZER

(75) Inventor: Kurt Weckstrom, Espoo (FI)

(73) Assignee: Instrumentarium Corp., Helsinki (FI)

( * ) Notice: Subject to any disclaimer, the term of this patent is extended or adjusted under 35 U.S.C. 154(b) by 89 days.

(21) Appl. No.: 10/102,566

(22) Filed: Mar. 20, 2002

(65) Prior Publication Data

US 2002/0137228 A1 Sep. 26, 2002

(30) Foreign Application Priority Data

Mar. 23, 2001 (EP) ............................................. 01660055
Sep. 21, 2001 (EP) ............................................. 01660175

(51) Int. Cl.$^7$ ............................................. G01N 21/76
(52) U.S. Cl. ..................... 436/116; 436/166; 436/172; 422/52
(58) Field of Search ................. 436/116, 117, 436/118, 166, 172; 422/52, 82.08, 84; 250/361 C

(56) References Cited

U.S. PATENT DOCUMENTS

| | | | |
|---|---|---|---|
| 3,856,473 A | * 12/1974 | Dillon | 422/52 |
| 4,333,735 A | * 6/1982 | Hardy et al. | 436/114 |
| 4,357,420 A | * 11/1982 | Bostick et al. | 435/8 |
| 4,822,564 A | 4/1989 | Howard | |
| 5,531,218 A | 7/1996 | Krebs | |
| 5,633,170 A | 5/1997 | Neti | |
| 5,792,326 A | 8/1998 | Harada et al. | |
| 5,976,889 A | * 11/1999 | Hirai et al. | 436/116 |
| 6,099,480 A | 8/2000 | Gustafsson | |
| 6,100,096 A | * 8/2000 | Bollinger et al. | 436/116 |
| 6,346,419 B1 | * 2/2002 | Ryerson et al. | 436/117 |
| 6,440,263 B1 | * 8/2002 | Li et al. | 156/345.12 |

FOREIGN PATENT DOCUMENTS

| | | |
|---|---|---|
| FR | 2495775 | 6/1982 |
| FR | 2612640 | 9/1988 |
| WO | 86/01296 | 2/1986 |
| WO | 97/31257 | 8/1997 |

OTHER PUBLICATIONS

"A General, Cryogenically–Based Analytical Technique for the Determination of Trace Quantities of Volatile Organic Compounds in the Atmosphere", Randolph A. Coleman et al., 1985 American Meteorological Society, pg. 273 277.

"A High–Sensitivity Combustible Gas Monitor Based on Dual Metal Oxide Semiconductor Sensors", Seajin Oh and Kenneth Johnson, Electrochemical Society Proceedings, vol. 97–19, pp. 770–778.

Patent Abstract of Japan, Publication No. 62215853, Sep. 22, 1987, "Apparatus for Measuring Ozone in Water", Aoki Toyoaki.

(List continued on next page.)

Primary Examiner—Jeffrey Snay
(74) Attorney, Agent, or Firm—Andrus, Sceales, Starke & Sawall, LLP

(57) ABSTRACT

This invention relates a chemiluminescent gas analyzer for determining a concentration of a gaseous component (G1) in a sample gas mixture (2). The analyzer comprises a measuring chamber (3), an ozonizer (4) with ozone generating devices (44) for producing ozone-containing gas (G2), input conduits (24, 23) for delivering the ozone-containing gas and said gas mixture into the chamber and an outlet (18). A detector (7) receives radiation (E) emitted as a consequence of a reaction between the gaseous component and the ozone-containing gas. Said analyzer further comprises a flow delay device (41) in or upstream the input conduit for said ozone-containing gas and downstream from the ozone generating devices (44) of the ozonizer. The flow delay device has a delay volume ($V_D$) causing a predetermined delay time (T) for the flow of the ozone-containing gas from said ozonizer to said measuring chamber (3).

34 Claims, 2 Drawing Sheets

OTHER PUBLICATIONS

Patent Abstract of Japan, Publication No. 10213578, Jan. 29, 1997, "Water Quality Analyzer", Iharada Kenji.

"Optimization of the Operating Parameters of Chemiluminescent Nitric Oxide Detectors", D. M. Steffenson and D.H. Stedman, Analytical Chemistry, vol. 46, No. 12, Oct. 1974, pp. 1704–1709.

"Modeling and Applications of Silent Discharge Plasmas", Baldur Eliasson and Elrich Kogelschatz.

"Zersetzung durch elektrische Entladusz e", Gmelins Handuch Der Anorganischen Chemie Stickstoffoxyd, p. 4, 1936.

* cited by examiner

CHEMILUMINESCENT GAS ANALYZER

CROSS REFERENCE TO RELATED APPLICATION

The present application claims priority from European Patent Application No. 01660055.3, filed Mar. 23, 2001 and European Patent Application No. 01660175.9, filed Sep. 21, 2001.

BACKGROUND AND SUMMARY OF THE INVENTION

The invention relates to a chemiluminescent gas analyzer for determining a concentration of a gaseous component in a sample gas mixture, comprising: a measuring chamber; input conduits for delivering an ozone-containing gas and said gas mixture into said chamber, and at least an outlet for removing said gaseous substances and possible chemical compounds thereof; radiation sensitive detector(s) receiving radiation emitted as a consequence of a reaction between the gaseous component and the ozone-containing gas; an ozonizer for producing said ozone-containing gas. The invention also relates to a method for determining a concentration of a gaseous component in a sample gas mixture, the method comprising the steps: generating an ozone-containing gas; allowing said ozone-containing gas and said gas mixture to stream into a measuring chamber and mix with each other; detecting an intensity of radiation emitted as a consequence of a reaction between the gaseous component and the ozone-containing gas; removing said gases and possible chemical compounds thereof from said chamber, as well as to a method for lowering the quantity of adverse chemiluminescent reactions in a measuring chamber fed by an ozone-containing gas and a sample gas mixture, whereupon a concentration of a gaseous component in said sample gas mixture is to be determined by detecting an intensity of radiation emitted as a consequence of reactions between the gaseous component and the ozone-containing gas.

Nitric oxide (=NO) can be measured in very small concentrations and with short response time using the chemiluminescence technique, whereupon ozone (=$O_3$) or ozone-containing gas is used as a reactant, i.e. here chemiluminescence occurs in a gaseous state. Gas phase chemiluminescent reactions occur also between ethylene and ozone, between carbon monoxide CO and atomic oxygen and between dimethylsulfid and fluorine $F_2$ forming hydrogen fluoride HF in excited state, etc. Since nitric oxide was found to be a signal substance in the body of human beings or animals it has been more and more important to be able to reliably measure nitric oxide entering or exiting the body. Most often nitric oxide is measured in breathing gas either in connection with treatment of lung disease or during asthma diagnostics and as a measure of response to a treatment. The normal requirement for this purpose is a sensitivity of about 1 ppb (parts per billion=$10^{-9}$), and a response time of about 200 ms for a breath-by-breath recording. The concentration of nitric oxide in the exhaust gases from internal combustion engines is also one area in which the chemiluminescence technique is utilized, but in this case a considerably lower sensitivity in the ppm range (parts per million=$10^{-6}$) is sufficient. Typical chemiluminescent gas analyzers are described in U.S. Pat. Nos. 4,822,564 and 6,099,480. As with any luminescence reaction, also in this kind of gas phase chemiluminescence the signal available is quenched by molecules of other gas components in the gas mixture measured. To minimize this harmful quenching of excitation, it is common practice to use very low pressure in the reactor chamber, where NO is reacting with ozone to form nitrogen dioxide in an excited state. The pressures in the reaction chambers are generally suggested to be below 0.01 bar. The chemiluminescent reaction should take place within the reaction chamber so that all created light could be detected. For a sample flow of about 200 ml/min this means that the reaction chamber has to be quite big, often more than 100 $cm^3$, whereupon the light collection has quite a low efficiency. So relatively high NO-concentrations, in the order of tens ppm, can generally be detected using the systems of the above-mentioned publications.

The ozone to be fed for attaining the chemiluminescent reaction is produced using an ozonizer with air as its input gas. The ozonizers are generally based on electrical discharge, preferably on a so called silent discharge, as described in the publication: IEEE Transactions on Plasma Science, Vol.19, No. 2, April 1991 (309–323)-B.

Eliasson and U. Kogelschatz *"Modeling and Applications of Silent Discharge Plasmas"*. In such a discharge ozone is generated from oxygen but also different oxides of nitrogen are produced interfering with ozone generation, which is disadvantageous for industrial ozone generation using large installations. According to the patent U.S. Pat. No. 5,792, 326 the ozone gas transport path is furnished with means for removing nitrogen oxides using a vessel filled either with an adsorbing zeolite material or dissolving pure water for passage of the gas in the form of tiny bubbles. Hence the object is to purify the ozone gas emerging from the ozonizer so that the ozone gas would be useful for semiconductor fabrication processes and problems caused by contamination with chromium, originating from stainless steel components, could be avoided. Because the ozone gas is here use for semiconductor fabrication processes the concentration of ozone should also be high. The purifying materials, like zeolite and water, require regular service and material changing at certain intervals. Additionally there are considerable material expenses.

It is known that ozone is a very reactive gas and so it can react with a number of different materials and constituents of materials and various other chemicals present. For example dirt and organic materials originating from a patient together with the sample gas often cause some chemiluminescent reactions, which is detected as a high dark level or background signal in the analyzer. The high dark level or background signal cannot be distinguished from the correct radiation mathematically, and so conducts to receiving erroneous concentration values. In the chemiluminescent gas analyzers, the light or radiation caused by this kind of unintended chemiluminescent reactions and/or the fluorescent radiation interfering with wavelengths utilized for the actual measuring of concentration is/are eliminated, if necessary, using an optical filter or optical filters between the measuring chamber and the detector or detectors, as shown in the non-published patent application EP-01660055.3 of the applicant. The optical filter(s) can be long pass filter(s), short pass filter(s), or band pass filter(s). E.g. in case nitric oxide NO reacting with ozone $O_3$ is measured, an optical long pass filter having transparence over about 620 nm is often used.

The object of the present invention is to improve the elimination of that possibly emitted weak light or radiation not proportional to the concentration of the gas component(s), which is/are measured utilizing ozone based chemiluminescent reactions in a measuring chamber. This means that the adverse effects of light or radiation caused by at least other than intended chemiluminescent reactions should be minimized. Another object of the present invention is to attain a small sized chemiluminescent analyzer with high sensitivity in respect to those wavelengths, which are excited by that or those chemiluminescent reaction(s) depending on the gaseous components to be measured in the sample gas mixture. Further an object of the present invention is to attain a chemiluminescent analyzer, which does not consume material and require frequent service, if only possible, at least for the purpose of lowering or eliminating high dark level or background signal.

The above-defined objects can be achieved by means of a chemiluminescent gas analyzer according to the invention comprising a flow delay device in the input conduit for said ozone-containing gas and downstream from the ozonizer, and said flow delay device having a delay volume causing a predetermined delay time for the flow of the ozone-containing gas from said ozonizer to said measuring chamber. Further, the above-defined objects can be achieved by means of a method for determining a concentration of a gaseous component in a sample gas mixture by delaying the flow of said ozone-containing gas between the generation thereof and said streaming into the measuring chamber with a predetermined delay time, or by means of a method for lowering the quantity of adverse chemiluminescent reactions, in which the flow of the ozone-containing gas is delayed so as to provide a predetermined delay time after the generation of the ozone in said ozone-containing gas and prior said reactions within the measuring chamber.

Now it has surprisingly noticed that a considerable portion of the high dark level or background signal is caused by the ozone-containing gas alone when entering the measuring chamber, at least in small sized analyzers, in the absence of any sample gas and any contamination. The possibility to this kind of light emission is confirmed by the publication: Gmelins Handbuch der Anorganischen Chemie, *Stickstoff*, Vol. 4, 1936 p. 628, which describes that the decomposition of NO in an ozonizer goes through three intermediate steps, whereupon the color of the emitted light changes from yellow at the first step, gradually through yellow-red and fiery red to blue-magenta at the end. Further it has surprisingly been noticed that the adverse effect of these spontaneous reactions on the measuring accuracy and reliability can be avoided by simply delaying the flow in the ozone line after the ozone generation so that the light producing reactions have time to fade out. The improvement according to the invention is to provide the delay time accomplished using a specific volume depending on the flow rate of the ozone-containing gas. As a result, the dark signal decreases to the same level as if no nitrogen oxides were present at all. The delaying volume can be in almost any form and material providing that no adsorption of the ozone occurs and that is resistive to the gases. So, according to the invention there is no need for trying to remove the nitrogen oxides, because they do not any more disturb the chemiluminescent measurement even in a sensitive analyzer. Further, there is no need for service concerning changing of material(s), since no part of the delay device is consumed.

BRIEF DESCRIPTION OF THE DRAWINGS

The invention is now described in detail with reference made to the accompanying drawings.

DETAILED DESCRIPTION OF THE INVENTION

Figure 1:
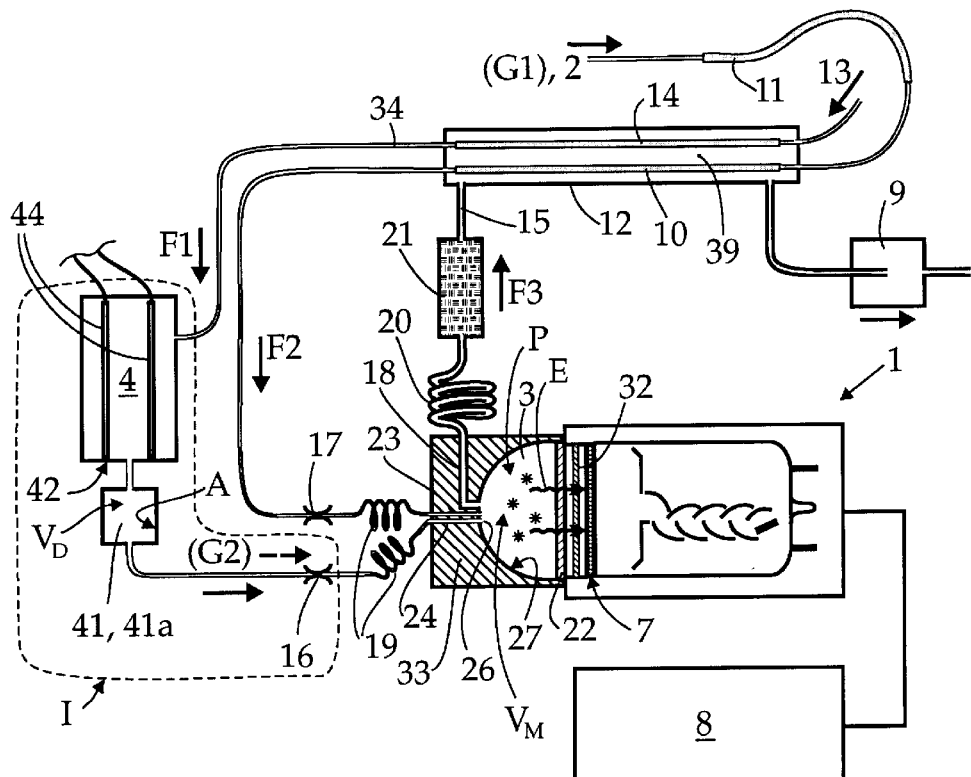
FIG. 1 illustrates generally the improved chemiluminescent gas analyzer with the first embodiment of the delay volume according to the present invention.

This invention is an improvement to the chemiluminescent gas analyzer disclosed in the non-published patent application EP-01660055.3 of the Applicant. With reference to FIG. 1 the main parts of a chemiluminescent gas analyzer 1 for determining the concentration of a gaseous component G1 in a sample gas mixture 2 is described below. For simplicity the description to follow is concerning measurement of nitric oxide NO as the gaseous component G1 in a gas mixture 2 like breathing air to or from a patient like human being or animal, and using ozone $O_3$ as a gaseous reagent in the ozone-containing gas G2. It shall be kept in mind that this does not intend any limitation, but the invention concerns analyzing the concentration of any gaseous component G1 in any kind of sample gas mixture 2 when using ozone as the reactant for obtaining the chemiluminescent reaction. The chemiluminescent reaction is arranged to occur in a measuring chamber 3 defined by a reflective inner surface 27 of a housing wall 33 and by a transparent window 22. The sample gas 2 containing NO is drawn or delivering into the measuring chamber 3 where it reacts with ozone $O_3$ from an ozone generator or ozonizer 4. In the reaction $NO_2$ is formed in an excited state of the electron shell. Part of the electrons in the excited states return to their ground state by emitting photons, that is radiation E, within the wavelength region between 600 nm and 3000 nm. The radiating emission process is indicated as small stars in the measuring chamber 3 for reaction. Input conduits 23 and 24 are connected to the measuring chamber for delivering the sample gas 2 including the gaseous component G1 like nitric oxide and the ozone into the measuring chamber in order to attain the chemiluminescent reaction therein. At least outlet 18 is also connected to the measuring chamber for removing said gases 2, G2 and possible chemical compounds thereof from the measuring chamber.

An amount of the excited radiation E is collected at a sensitive area of the radiation sensitive detector or detectors 7 directed to said window and to the interior or volume $V_M$ of said measuring chamber, and it receives radiation emitted as a consequence of a reaction between the gaseous component G1 and the ozone-containing gas G2. Photon counting is normally applied to reduce the noise level. The photon pulses are counted and the analyzer calibrated to show nitric oxide NO concentration in a conventional electronic unit 8 of the instrument performing the necessary calculations. As long as enough ozone is provided for the reaction or, alternatively, the ozone concentration is kept at a constant level, the produced signal will be a linear function of the NO concentration. At very high counting rates the detector may gradually be saturated because of an increasing dead time, but this does not happen at ppb levels of NO mainly considered in this invention.

The reflective inner surface 27 of the measuring chamber 3 in this improved chemiluminescent gas analyzer 1 is substantially or mainly composed of convergent surface sections each having preferably also a substantially concave configuration, extending in direction from said transparent window 22 towards a bottom of the chamber. In general the reflective inner surface is so at least for the main part tapering towards the bottom of said chamber. The bottom of the measuring chamber is at a point of the inner surface 27 far off from the window, preferably at the furthest point or end of the chamber as seen in the direction of a normal to the window. Those possible sections not convergently tapering towards the bottom, i.e. cylindrical or parallelepipedous or any surface form are positioned next or close to the window. Convergence of the surface sections means that the successive cross-sectional areas of the reflective inner surface 27 are continuously decreasing in direction towards the bottom, when the cross-sections are formed by planes parallel to the window 22. Preferably the number of these planes can increase limitless. So the convergent surface section(s) are efficiently light collecting. Further according to the invention, the input conduit 23 for the sample gas 2 has at least one orifice, and the input conduit 24 for the ozone-containing gas G2 has at least one orifice 26 within a bottom end region of the measuring chamber which region is opposite to said window. Both the sample gas 2 and the ozone $O_3$ contained in the air coming from the ozonizer 4 stream either simultaneously or successively into the measuring chamber 3 and mix in the chamber with each other under a pressure P, which is lower than the standard atmospheric pressure during radiation detection by said detector 7. During this mixing the chemiluminescent reaction between the ozone and the nitric oxide is occurring and radiation E excited. The conditions in the measuring chamber are discussed next. Also the outlet 18 opening(s) is/are preferably within the bottom end region of the chamber 3 for removing the gases and the possible chemical compounds from the chamber.

The flow inside the measuring chamber 3 will grow as the pressure is reduced and, as a consequence, a larger and larger measuring chamber will be needed to contain the reaction totally while it lasts. The reaction time is only about 10 ms but the mixing time can be much longer and at a pressure of less than 0.05 bar the chamber volume must typically be more than 100 cm$^3$, as in the prior art publications, to avoid the continuation of mixing and chemiluminescent reaction in the outlet tube outside the chamber. In this improved chemiluminescent gas analyzer 1 the volume $V_M$ of the measuring chamber 3 can be less than 10 cm$^3$ for pressures P above 0.2 bar within the chamber 3. Measurements have shown that volume $V_M$ of 2.4 cm$^3$ is optimal at pressure P of 0.5 bar. It is much easier to collect the chemiluminescent light from a small chamber than from a large one. As far as it is understood, the measuring chamber has an optimum pressure P of at least 0.3 bar or over 0.3 bar and below 0.6 bar, but somewhat lower pressure P down to 0.2 can be used as well as somewhat higher pressures like 0.7 bar at maximum, or even up to 0.9 bar at maximum. Above that optimum the reaction starts being quenched because of the pressure and below the optimum pressure the chamber volume is too high, and the unfinished reaction is flushed out before detection. In general, volumes V smaller than 10 cm$^3$ but larger than 1.2 cm$^3$ can be used, and preferably the volume V is between 5 cm$^3$ and 2 cm$^3$. Therefore, it is preferable to use measuring chamber pressures at least 0.2 bar, preferably at least 0.4 bar, or in the range between 0.4 bar and 0.5 bar. All the other features and benefits described in this improved chemiluminescent gas analyzer 1 are also based on the fact that pressures higher than 0.2 bar are used. In this kind of measuring chamber the mixing of the sample gas and the ozone still happens close enough to the window but without influence on the window. The used pressure level also reduces the requirements on hoses and joints by making leak problems less critical, and further enable use of smaller light traps and smaller pumps. Additionally, stray light reduction is easier to implement with suitable simple light traps at the inlets and outlet to the measuring chamber because of the smaller tube dimensions. Altogether a small, inexpensive and very sensitive NO-analyzer results. The analyzer further comprises a flow resistance 16 in the input conduit 24 for said ozone-containing gas G2 and a flow resistance 17 in the input conduit 23 for said sample gas 2 for attaining a proper pressure P and flow in the measuring chamber.

The main benefits from using measuring chamber 3 with internal pressures P at least or higher than 0.2 bar are related to the chamber itself, its construction and the components attached thereto. With pressure according to the invention it is possible to optimize the measuring chamber 3 so that it has as small an inner area of the reflective inner surface 27 as possible for the volume $V_M$ of the chamber 3 and the active area of the detector 7. Also it is beneficial if the main part of the light either hits the active area of the detector 7 directly, i.e. without any reflection, or after only one reflection from the wall surface 27. In other words, the excited radiation E is collected for detection so that a substantial portion of that radiation not directly hitting the active area of detector 7 is allowed to reflect once only before hitting said active area. This is even more important if the reflectivity of the chamber walls decreases as a consequence of dirt and corrosion. For all rays emitted in the hemisphere directed away from the detector one reflection is imperative in order to change the direction but already a second reflection starts to increase the losses in the signal. In the case of a half sphere 52% of all these rays are turned towards the detector after one reflection. The corresponding number for the cylindrical reflective surface with planar bottom of the prior art is only 24%. After one or two reflections the numbers were 77% and 60%, respectively. If any number of reflections is allowed and the wall reflectivity is 0.9 the half sphere gives 12% more total signal than the cylinder. The surface area difference would indicate an increase of about 14%. The numbers do not match since a large amount of the radiation hits the detector directly independently of the surface shape.

It is preferred that the window 22 constitutes the optical filter, i.e. the window is the filter 22, between the measuring chamber and said radiation sensitive detector in case such an optical filter is used in the analyzer 1. If practical a separate filter 32 between said window and the detector can be used. In case NO reacting with ozone $O_3$ is measured, an optical long pass filter having transparence over about 620 nm can be used, but for measuring other kind of reactions a different optical filter may be utilized or the optical filter can be left away. The reason for this is that disturbing fluorescence because of a reaction between ozone and dirt may increase the signal background or cause signal drift.

A sample pump 9 is used to provide a suitable sample gas flow F2 to the measuring chamber 3, carrier gas flow F1 through the ozonizer 4 into the measuring chamber 3 and exit gas 15 flow F3 out of the measuring chamber 3. The ozone $O_3$ generator or ozonizer 4 is arranged in a feeding conduit 34 downstream from a second hygroscopic ion exchange tube 14 and prior to the input conduit 24 leading into the measuring chamber. The pump 9 is connected to suck the gases from the measuring chamber and through the scavenger 21 as well as through demoisturizing unit or drier 12 described later in this text. Since the volume $V_M$ of the measuring chamber is small rendering also small existing gas flows F1, F2, F3 which are utilized also for the drier 12 and a predrier 11, the pump capacity can be kept at a low level and the pump 9 can be small, inexpensive and silent. In the pre-drying third hygroscopic ion exchange tube 11 the saturated respiratory sample gas 2, G1 is predemoisturized so that its water partial pressure reduces to that of the ambient conditions around the third hygroscopic ion exchange tube 11. This third hygroscopic ion exchange tube 11 is in series with and in flow direction F2 prior to a first hygroscopic ion exchange tube 10. The room inside the drier 12 is connected to flow F3 of the exit gas 15, whereupon there is the same vacuum or pressure P lower than standard atmospheric pressure produced by pump 9 as in the measuring chamber 3. This exit gas 15 has a reduced water partial pressure relative to its lower pressure from its original pressure, and further the exit gas are the same gases fed as flows F2 and F1 through the input side of a first hygroscopic ion exchange tube 10 and a second hygroscopic ion exchange tube 14 respectively within the drier 12 and so demoisturized and predemoisturized reducing the water partial pressure in the input gas flows F1, F2 to the same level as the exit gas 15 flow F3. The first exchange tube 10 is positioned in the input conduit 23, and the outlet 18 from said measuring chamber is in counter flow F1, F2 ⇔ F3—because input flows F1, F2 are opposite to the exit flow F3—communication with exhaust sides 39 of the first exchange tube 10. The dryer 12 in the feeding conduit 34 is preferably connected and constructed also to dry the air 13 received prior to flowing to the ozonizer 4 by utilizing the second hygroscopic ion exchange tube 14, which second exchange tube 14 is in the feeding conduit 34.

Both input conduits 23 and 24 are fitted with light trap tubes 19 and the outlet(s) 18 has/have its/their own light trap tube(s) 20 of slightly larger dimension in order not to restrict the flow to the vacuum pump 9. A scavenger and if necessary a scrubber 21 removes the unused ozone $O_3$ and the nitrogen dioxide $NO_2$ from the flow F3 of the exit gases 15 so that the reactive nature of ozone does not interfere with the structures of the pump 9 or cause harm to the environment, and so that the poisonous nitrogen dioxide does not cause harm to the environment. The input gases, i.e. air 13 into the ozonizer 4 and the sample gas mixture 2, can be pre-filtered to remove dust, water and mucus, and at the output there can be a filter absorbing the produced nitrogen dioxide.

Figure 6:
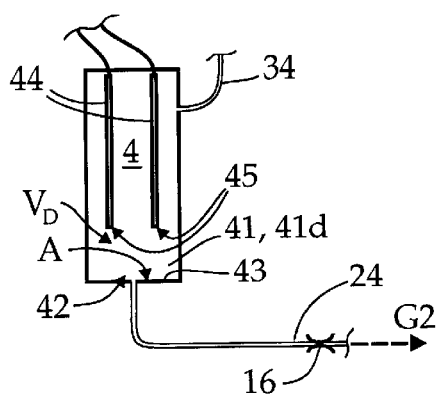
Figure 7:
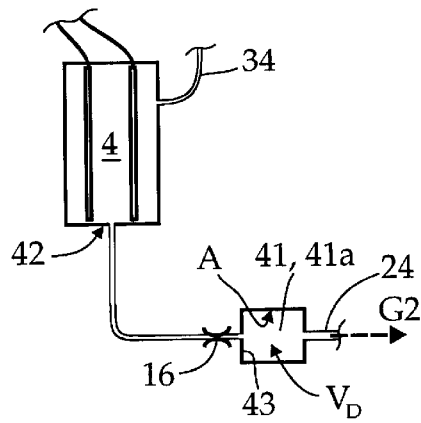
FIG. 7 illustrates the fifth embodiment and disclosing a different position of the delay volume according to the present invention, corresponding to the area I of FIG. 1.

The improved analyzer 1 according to the invention further comprises a flow delay device 41 either in the input conduit 24 for the ozone-containing gas G2, as shown in FIGS. 1, 4 to 5 and 7, or upstream the input conduit 24 for the ozone-containing gas G2 and so opening into this input conduit, as shown in FIG. 6, and further the flow delay device is inserted downstream from the ozonizer 4 and preferably in front of the flow resistance 16. A reference number 41 is used for this delay device when discussed generally, and the detailed reference numbers 41a, 41b, 41c etc. are used only when a specific type of delay device 41 is considered. This delay device 41 should have a specific volume $V_D$ determined by the required delay time T for the flow of the ozone-containing gas G2 from said ozonizer 4 to said measuring chamber 3 and by the flow rate of the ozone-containing gas G2. In other words, the flow of said ozone-containing gas G2 is delayed with a predetermined delay time T between the generation thereof and the streaming into the measuring chamber 3 through the orifice 26, and this delay time is formed by a predetermine delay volume $V_D$. Typically, this volume $V_D$ would be between 1 and 100 cm$^3$ with a predetermined delay time T requirement in the range of 1 second to 100 seconds. If the ozone $O_3$ in the gas G2 is not consumed by adsorption or any chemical reaction the delay time and, subsequently, the volume can be still larger, but in a small sized analyzer nothing is gained from increasing the volume beyond a certain value. By using this type of increased time span after the generation of the ozone $O_3$ in said ozone-containing gas and prior the chemiluminescent reactions within the measuring chamber 3 fed by an ozone-containing gas G2 and a sample gas mixture 2, the quantity of adverse chemiluminescent reactions in the measuring chamber can be considerably lowered, whereupon a concentration of a gaseous component G1 in said sample gas mixture can be determined more reliably and accurately. This will be evident further below.

The ozonizer 4 has one or several plates and/or parts with other form and/or conductive areas in these plates or other parts acting as ozone generating means 44, whereupon a high electrical voltage is provided into these ozone generating means 44, e.g. between these plates and/or parts and/or areas, so producing ozone from the air 13 fed into the ozonizer as a carries gas. The construction and operation of ozonizers are generally known, and they are not explained more in detail in this text. The active, i.e. high-voltage carrying sections of the ozone generating means, like the plates, parts and areas, have end point or points 45 in the flow direction of the carrier gas, after which end point(s) there is no sections of the ozone generating means carrying a high-voltage in the ozonizer 4 contributing ozone formation. The delay volume $V_D$ and the delay time T of the delay device 41 according to the invention shall be considered to extend downstream from the point(s) of the last active sections provided with the high-voltage, and so downstream from the ozone generating means 44, more specifically downstream from said end point(s) 45. It shall be understood that the delay device 41 may include carrying or fastening elements for the active sections of the ozone generating means or parts, but the delay device does not include those active sections.

Figure 2:
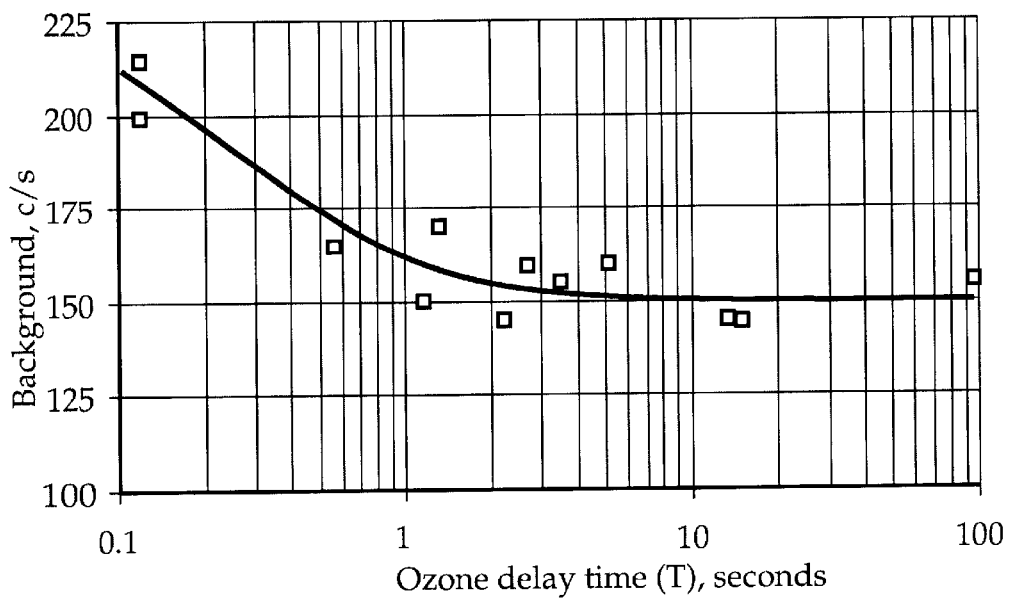
FIG. 2 shows graphically the dependence between the delay time in the flow of the ozone-containing gas and the background or dark signal based on measurements using different delay volumes between the ozonizer and the measuring chamber.

FIG. 2 illustrates the background or dark signal in counts/seconds as a function of the delay time T of the ozone-containing gas G2 after the generation of the ozone $O_3$ in seconds without any activated gaseous component G1 in the sample gas 2, or alternatively without any sample gas 2. Many different types of delay devices 41; 41a, 41b, 41c, 41d have been used to produce the measured points in the diagram. The first points to the left represent the delay time from the universally used short connection tubing, whereupon the problematic increased dark level especially related to compact NO analyzers is visible. It can be seen that after about a delay time T of 1 second the dark signal starts to level off to a reduced value. This process is finished after about 10 seconds of delay time T. A longer delay time T does not reduce the dark level any further and would only increase the space needed for the volume of the device. The utility signal levels in counts/200 ms, and in the presence of 1 ppm NO as the gaseous component G2 in the sample gas 2, are then like those of the measured points to the very left in FIG. 3. The ozone time delay does not have to be more than about 10 seconds depending on conditions in order to practically nullify the phenomenon of increased dark level and decrease of the utility signal level. With a volume flow of 80 ml/min of the ozone-containing gas G2 the needed delay volume $V_D$ would be about 10 cm³ concerning the embodiments of FIG. 1 and FIGS. 4 to 6. The diagrams indicate that this volume could be even more than 100 cm³, but such a volume does not give any benefits. The delay volume $V_D$ concerning the embodiment of FIG. 7 would be about considerably larger, typically several times the delay volume of embodiments of FIG. 1 and FIGS. 4 to 6, because the pressure in the delay device is lower and so the volume flow higher. The delay time T is that which matter in any case. Anyway depending the conditions and the requirements the predetermined delay time T is arranged or controlled to be at least 0.5 seconds, or preferably at least 1 second. The minimum of said predetermined delay time T can be extended to be at least 2 seconds. The most important feature of the invention is that the delay time T exceeds a predetermined minimum time. It is practical requirement that the predetermined delay time T is arranged or controlled to be at maximum 20 seconds, or at maximum 10 seconds. The maximum time primarily affects the size of the delay device and so the space needed, but if excessively large, may also bring harmful effects. A too big vessel would slow down the initial ozone build-up and could even start to consume ozone as a consequence of adsorption or catalytic or other chemical reactions without emission of light, and of course may hamper the obtaining of a compact design.

The control of the predetermined delay time T is performed by a constant predetermined delay volume $V_D$ of the delay device 41. Physically, the delay device 41 can have any form that fulfills the volume requirements and the material of which is resistive to ozone and nitrogen compounds. At least some polymers, like PVDF and PTFE, are found to be useful, and so some metals, like aluminum, or alloys are found to be useful, too. Concerning the form or construction, the flow delay device 41 can be a can 41a, as in FIGS. 1 and 7, or an extended or longer and/or wider than normal tubing 41b, as in FIG. 4, or a bottle 41c, as in FIG. 5, or an extension 41d at an output end 42 of the ozonizer 4, i.e. part of the ozonizer at its output as shown in FIG. 6, or another kind of vessel between the ozonizer 4 and the input orifice 26 opening into said measuring chamber 3. Said flow delay device 41 has preferably a predetermined minimum internal area A as regards to the delay volume $V_D$ of said flow delay device, in order to avoid any catalytic effect possible. Different sizes and forms of tubing, cans, bottles, and vessels have been tested with the result that the main influencing parameter is the delay time T in the flow of the ozone-containing gas G2. It is important that the flow delay device 41 has, as far as possible, substantially nonreactive and noncatalytic inner surfaces 43 and also substantially nonabsorptive and nonadsorptive inner surfaces 43. Because ozone is very reactive gas it shall be noticed that some reaction may happen with the wall material of delay device 41, whereupon the delay time T is caused by the delay volume $V_D$ constructed from materials approaching nonabsorptive and nonadsorptive properties as well as approaching nonreactive and noncatalytic properties in contact with said ozone-containing gas G2. Possible reactions between gaseous oxides and/or oxygen $O_2$ and/or ozone $O_3$, i.e. between the prevailing components of the ozone-containing gas G2, are allowed to happen spontaneously during said predetermined delay time T without added reactants or without added catalysts and without materials with substantial absorption or adsorption properties, and also without withdrawing any of those prevailing components, meaning that no purification of the ozone-containing gas G2 is performed.

As mentioned, the adverse background signal is decreased considerably and the utility signal and thus the sensitivity are increased up to a level corresponding to a delay time T of about 10 seconds in the method and apparatus according to invention. The reason for these effects are not clearly understood but the need for temporal delay of the ozone-containing gas G2 in order to reduce the influence originating from nitrogen oxides initially present in this gas G2 after ozone formation is believed to be related to the reactions explained below. The different chemical species generated by a microdischarge in air are shown in the earlier mentioned article: B. Eliasson and U. Kogelschatz—*Modeling and Applications of Silent Discharge Plasmas*. After about 10 ms the main generated gas components in air are ozone $O_3$, nitrous oxide $N_2O$, and nitrogen dioxide $NO_2$, hereafter the concentration of $NO_2$ lowers to a negligible level as that of $NO_3$ and, finally $N_2O_5$ increases. The earlier mentioned publication: Gmelins Handbuch der Anorganischen Chemie—*Stickstoff* reports emission of light with gradually changing colors. So, it might be possible that the generated $NO_2$ is in an excited state and is able to emit weak light in the spectral region used by the NO-analyzer, and the emitted light might be capable to transmit through the color filter 32, 22 of the chemiluminescent analyzer, thus influencing the reading.

Figure 3:
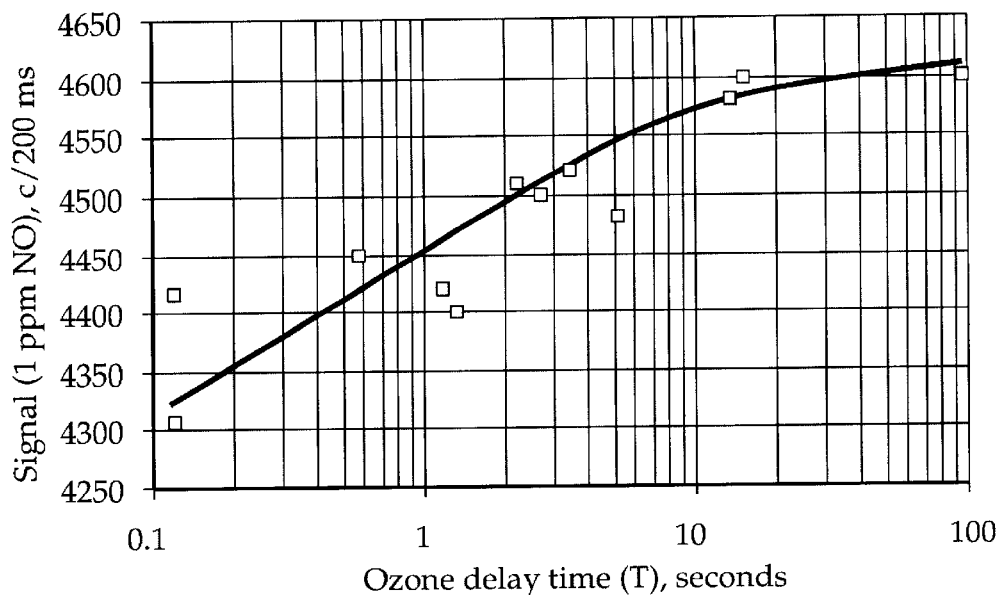
FIG. 3 shows graphically the dependence between the delay time in the flow of the ozone-containing gas and the signal concerning nitric oxide NO in the sample gas.
Figure 4:
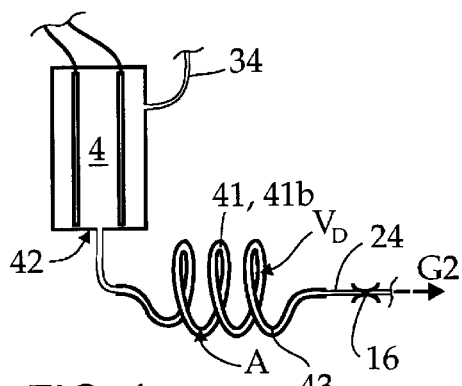
FIGS. 4 to 6 illustrate the second, the third, the fourth embodiments respectively and disclosing the various forms and preferred positions of the delay volume according to the present invention, corresponding to the area I of FIG. 1.
Figure 5:
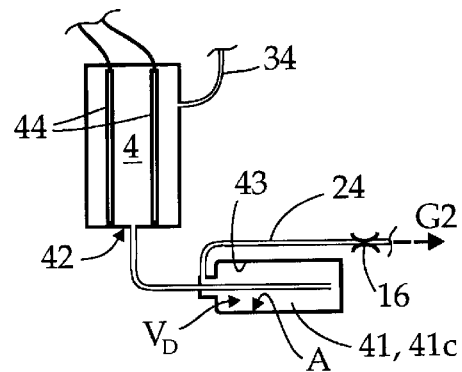

The explanation for the increased sensitivity as shown in FIG. 3 could be that the unfinished reactions described above normally deprive the gas to be measured of NO molecules. The situation is normalized after the addition of the flow delay device 41 providing the delay time T described.

As shown in FIG. 2 a lowering of about one third of the dark level can be gained using the delay device 41 of the invention. There will still be a small ozone depending background contribution despite of the optical filter 32 but this cannot be eliminated in this invention, because it is not related to nitrogen oxides but to other reactions involving ozone. Therefore, it is advantageous to keep the ozone concentration at the lowest possible level for reliable NO measurements. The ozone $O_3$ concentration in the ozone-containing gas G2 shall be at least equal with the stoichiometric concentration thereof necessary for the maximum nitric oxide NO concentration or concentration of the gaseous component G1 in the sample gas mixture, the concentration of which shall be measured or can be present in the sample gas 2. Preferably the concentration of ozone in the ozone-containing gas G2 should be slightly higher than the its respective stoichiometric concentration. Too high ozone concentration can increase the background radiation or dark level without any increase in the utility signal. When using the delay device according to the invention, the sensitivity of detection is increased by about 6% according to the measurements shown in FIG. 3.

Above has been described how a compact but still very sensitive NO-analyzer can be improved by adding a delay device in the gaseous reagent line. To those skilled in the art it is obvious that also other embodiments and uses applying to the presented basic ideas are possible. Those skilled in the art can also understand that the inventive delay device and the respective method is also functional in circumstances with different pressure as compared to those described and in other kind of analyzers utilizing ozone for a specific reaction, which or the consequences of which is/are then detected.

What is claimed is:

1. A chemiluminescent gas analyzer for determining a concentration of a gaseous component in a sample gas mixture, comprising:

a measuring chamber;

input conduits for delivering an ozone-containing gas and said gas mixture into said chamber, and at least an outlet for removing said gaseous substances and possible chemical compounds thereof;

radiation sensitive detector(s) receiving radiation emitted as a consequence of a reaction between the gaseous component and the ozone-containing gas;

an ozonizer with ozone generating means for producing said ozone-containing gas; and a flow delay device in or upstream the input conduit for said ozone-containing gas and downstream from said ozone generating means of the ozonizer, said flow delay device having a delay volume to cause a predetermined delay time for the flow of the ozone-containing gas from said ozonizer to said measuring chamber.

2. A chemiluminescent gas analyzer according to claim 1, wherein said predetermined delay time is at least 0.5 second.

3. A chemiluminescent gas analyzer according to claim 2, wherein said predetermined delay time is at least 1 second.

4. A chemiluminescent gas analyzer according to claim 3, wherein said predetermined delay time is at least 2 seconds.

5. A chemiluminescent gas analyzer according to claim 1, wherein said delay time is at maximum 20 seconds.

6. A chemiluminescent gas analyzer according to claim 1, wherein said flow delay device is a can, or an extended tubing, or a bottle, or an extension at an output end of the ozonizer; said can or tubing or bottle or extension being between the ozonizer and an input orifice opening into said measuring chamber.

7. A chemiluminescent gas analyzer according to claim 1, wherein said flow delay device has a predetermined minimum internal area as regards the delay volume of said flow delay device.

8. A chemiluminescent gas analyzer according to claim 1, wherein said flow delay device has substantially nonreactive and noncatalytic inner surfaces.

9. A chemiluminescent gas analyzer according to claim 8, wherein said flow delay device has substantially nonabsorptive and nonadsorptive inner surfaces.

10. A chemiluminescent gas analyzer according to claim 1, wherein said analyzer further comprises a flow resistance in the input conduit for said ozone-containing gas, and said flow delay device is positioned between said flow resistance and said ozonizer.

11. A chemiluminescent gas analyzer according to claim 1, wherein the ozonizer has a feeding conduit connected to receive air as a carrier gas for the ozone-containing gas, and a dryer in said feeding conduit for drying said air prior to flowing to said ozonizer.

12. A chemiluminescent gas analyzer according to claim 1, wherein the pressure within the measuring chamber is at least 0.2 bar; and the measuring chamber has a volume smaller than 10 $cm^3$.

13. A chemiluminescent gas analyzer according to claim 12, wherein the pressure within the measuring chamber is at least 0.3 bar, and at maximum 0.9 bar.

14. A chemiluminescent gas analyzer according to claim 12, wherein the measuring chamber has a volume between 5 $cm^3$ and 1.2 $cm^3$.

15. A method for determining a concentration of a gaseous component in a sample gas mixture, the method comprising the steps:

generating an ozone-containing gas;

allowing said ozone-containing gas and said gas mixture to stream into a measuring chamber and mix with each other;

detecting an intensity of radiation emitted as a consequence of a reaction between the gaseous component and the ozone-containing gas;

removing said gases and possible chemical compounds thereof from said chamber; and delaying the flow of said ozone-containing gas between the generation thereof and said streaming into the measuring chamber with a predetermined delay time.

16. A method according to claim 15, wherein said predetermined delay time is controlled to be at least 0.5 seconds.

17. A method according to claim 16, wherein said predetermined delay time is controlled to be at least 1 second.

18. A method according to claim 17, wherein said predetermined delay time is controlled to be at least 2 seconds.

19. A method according to claim 15, wherein said predetermined delay time is controlled to be at maximum 20 seconds.

20. A method according to claim 19, wherein said predetermined delay time is controlled to be at maximum 10 seconds.

21. A method according to claim 15, wherein said controlling of the predetermined delay time is performed by a constant predetermine delay volume downstream from said generation of the ozone-containing gas.

22. A method according to claim 15, wherein possible reactions between gaseous oxides and/or oxygen and/or ozone are allowed during said predetermined delay time without added reactant(s) or without added catalyst(s).

23. A method according to claim 15, wherein said predetermined delay time is caused without materials with substantial absorption or adsorption properties in contact with said ozone-containing gas.

24. A method according to claim 15, wherein the sample gas mixture is a breathing gas to or from a patient; and said gaseous component is nitric oxide.

25. A method according to claim 15, wherein air is fed for generation of said ozone-containing gas.

26. A method for lowering the quantity of adverse chemiluminescent reactions in a measuring chamber fed by an ozone-containing gas and a sample gas mixture, whereupon a concentration of a gaseous component in said sample gas mixture is to be determined by detecting an intensity of radiation emitted as a consequence of reactions between the gaseous component and the ozone-containing gas, said method comprising the step of: delaying the flow of the ozone-containing gas so as to provide a predetermined delay time after the generation of the ozone in said ozone-containing gas and prior said reactions within the measuring chamber.

27. A method according to claim 26, wherein said predetermined delay time is arranged to be at least 0.5 seconds.

28. A method according to claim 27, wherein said predetermined delay time is arranged to be at least 1 second.

29. A method according to claim 26, wherein said predetermined delay time is arranged to be at maximum 20 seconds.

30. A method according to claim 29, wherein said predetermined delay time is arranged to be at maximum 10 seconds.

31. A method according to claim 26, wherein possible reactions between the prevailing components of the ozone-containing gas are allowed spontaneously during said predetermined delay time without activation and without withdrawing any of those components.

32. A method according to claim 26, wherein the sample gas mixture is a breathing gas to or from a patient; and said gaseous component is nitric oxide.

33. A method according to claim 26, wherein said ozone-containing gas is generated from air.

34. A method according to claim 26, wherein said predetermined delay time is formed by a predetermine delay volume downstream from said generation of the ozone-containing gas.

* * * * *